United States Patent
Lee et al.

(10) Patent No.: US 7,488,596 B2
(45) Date of Patent: Feb. 10, 2009

(54) MICROFLUIDIC DEVICE COMPRISING ELECTROLYSIS DEVICE FOR CELL LYSIS AND METHOD FOR ELECTROCHEMICALLY LYSING CELLS USING THE SAME

(75) Inventors: Hun-joo Lee, Seoul (KR); Joon-ho Kim, Gyeonggi-do (KR); Chang-eun Yoo, Seoul (KR); Hee-kyun Lim, Gyeonggi do (KR); Kyu-youn Hwang, Incheon-si (KR); Soo-min Ma, Gyeonggi-do (KR); Jun-hong Min, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 289 days.

(21) Appl. No.: 11/304,083

(22) Filed: Dec. 15, 2005

(65) Prior Publication Data

US 2006/0134777 A1    Jun. 22, 2006

(30) Foreign Application Priority Data

Dec. 17, 2004 (KR) .................. 10-2004-0108032
Jul. 21, 2005 (KR) .................. 10-2005-0066353

(51) Int. Cl.
*C12M 1/33*   (2006.01)
*C12M 1/34*   (2006.01)
*C12Q 1/70*   (2006.01)
*C12N 1/06*   (2006.01)

(52) U.S. Cl. .................. 435/306.1; 435/259; 435/287.1; 435/5

(58) Field of Classification Search .................. None
See application file for complete search history.

(56) References Cited

U.S. PATENT DOCUMENTS

| 2001/0034435 A1 | 10/2001 | Nochumson et al. ....... 536/23.1 |
| 2002/0197637 A1 | 12/2002 | Willson, III et al. ............ 435/6 |
| 2003/0075446 A1 * | 4/2003 | Culbertson et al. .......... 204/451 |

FOREIGN PATENT DOCUMENTS

| EP | 1 462 519 A1 | 9/2004 |
| WO | WO 99/25816 | 5/1999 |
| WO | WO 03/011768 | 2/2003 |
| WO | WO 2004/108287 | 12/2004 |

OTHER PUBLICATIONS

Huang Y and B Rubinsky. Microfabricated electroporation chip for single cell membrane permeablization. Sens Actuators A. 2001;89:242-249.*

(Continued)

*Primary Examiner*—Mary E Mosher
*Assistant Examiner*—Stuart W Snyder
(74) *Attorney, Agent, or Firm*—Cantor Colburn LLP

(57) ABSTRACT

Provided are a microfluidic device including an electrolysis device for cell lysis which includes an anode chamber, a cathode chamber and a separator, in which the separator is installed between the anode chamber and the cathode chamber, the anode chamber includes an inlet and an outlet for an anode chamber solution and an electrode, and the cathode chamber includes an inlet and an outlet for a cathode chamber solution and an electrode, and a method of electrochemically lysing cells using the same.

15 Claims, 11 Drawing Sheets

OTHER PUBLICATIONS

Lagally, et al. Integrated Portable Genetic Analysis Microsystem for Pathogen/Infectious Disease Detection. Anal. Cham. 2004;76:3162-3170.*

European Search Report for Application No. 05027643.5; Dated: Apr. 21, 2006 (All references cited in the Search Report are cited above).

* cited by examiner

MICROFLUIDIC DEVICE COMPRISING ELECTROLYSIS DEVICE FOR CELL LYSIS AND METHOD FOR ELECTROCHEMICALLY LYSING CELLS USING THE SAME

CROSS-REFERENCE TO RELATED PATENT APPLICATION

This application claims the benefit of Korean Patent Application No. 10-2004-0108032, filed on Dec. 17, 2004, in the Korean Intellectual Property Office, the disclosure of which is incorporated herein in its entirety by reference.

BACKGROUND OF THE INVENTION

1. Field of the Invention

The present invention relates to a microfluidic device comprising an electrolysis device for cell lysis and a method of lysing cells using the same.

2. Description of the Related Art

A microfluidic device refers to a device in which an inlet, an outlet, a reaction vessel, etc. are connected through microchannels. Such a device is well-known in the art and is widely used in microanalysis device such as a Lab-on-a-chip (LOC). In the microfluidic device, only the microchannels are not formed, but a micropump for transport and mixing of fluids, a micromixer, and a microfilter for filtering fluids which are being transported are also included. The microfluidic device used as a bioassay device such as the LOC generally should include equipments required in the procedure of lysing cells or viruses or use a cell solution lysed outside or already purified materials. An alkali method etc. was conventionally used as a cell lysis method. However, when using these methods, chemicals such as NaOH must be added and an equipment for removing the added chemicals after lysing cells mixed with chemicals must be included. For example, a valve, a pump, a filter and so on for performing the above procedure must be included.

Thus, a microfluidic device including an electrolysis device for cell lysis is not yet known.

In addition, various cell lysis methods are known. For example, a boiling method, an alkali method, a cell lysis method using an enzyme, etc. are known. The alkali method is a method of lysing cells by exposing cells or viruses to a material with high pH, such as NaOH. However, conventional cell or virus lysis methods such as the alkali method had many disadvantages to be used in micrifluidic devices such as the LOC. For example, when an alkaline cell lysate obtained by lysing cells using an alkaline solution such as NaOH is neutralized with a neutralization solution, an injection step of the alkaline solution for cell lysis and a device therefor are required and a sample solution is diluted due to addition of the alkaline solution and the neutralization solution. The solution injection step and the device can cause serious problems in the microfluidic device handling microvolumes and the dilution can cause problems when obtaining or amplifying the desired sample. Further, the alkaline solution such as NaOH must be removed or neutralized to be used in the subsequent biological analysis methods, such as PCR.

Thus, a cell lysis method capable of providing a cell lysate having suitable pH and conditions for the subsequent biological analysis while lysing cells by in situ generating a material which lyses cells, such as hydroxide through electrolysis is not yet known.

The inventors discovered that when electrolysis is performed using an anode chamber which contains an electrolyte including ions with lower or higher standard oxidation potential than water and a cathode chamber which contains an electrolyte including ions with a lower standard reduction potential than water and cells, a cell lysate having suitable pH and conditions for the subsequent biological analysis can be prepared, and thus led to completion of the present invention.

SUMMARY OF THE INVENTION

The present invention provides a microfluidic device including an electrolysis device for cell lysis.

The present invention also provides a method of lysing cells using electrolysis.

According to an aspect of the present invention, there is provided a microfluidic device comprising an electrolysis device for cell lysis which includes an anode chamber, a cathode chamber and a separator, wherein the separator is installed between the anode chamber and the cathode chamber, the anode chamber includes an inlet and an outlet for an anode chamber solution and an electrode, and the cathode chamber includes an inlet and an outlet for a cathode chamber solution and an electrode.

According to another aspect of the present invention, there is provided a method of lysing cells or viruses using a microfluidic device comprising an electrolysis device for cell lysis which includes an anode chamber, a cathode chamber and a separator, wherein the separator is installed between the anode chamber and the cathode chamber, the anode chamber includes an inlet and an outlet for an anode chamber solution and an electrode, and the cathode chamber includes an inlet and an outlet for a cathode chamber solution and an electrode, the method comprising:

introducing the anode chamber solution including a compound having lower or higher standard oxidation potential than water into the anode chamber through the inlet of the anode chamber;

introducing the cathode chamber solution including cells or viruses and a compound having lower standard reduction potential than water into the cathode chamber through the inlet of the cathode chamber; and lysing cells by applying current to electrodes included in the anode chamber and the cathode chamber to cause electrolysis in the anode chamber and the cathode chamber.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1A:
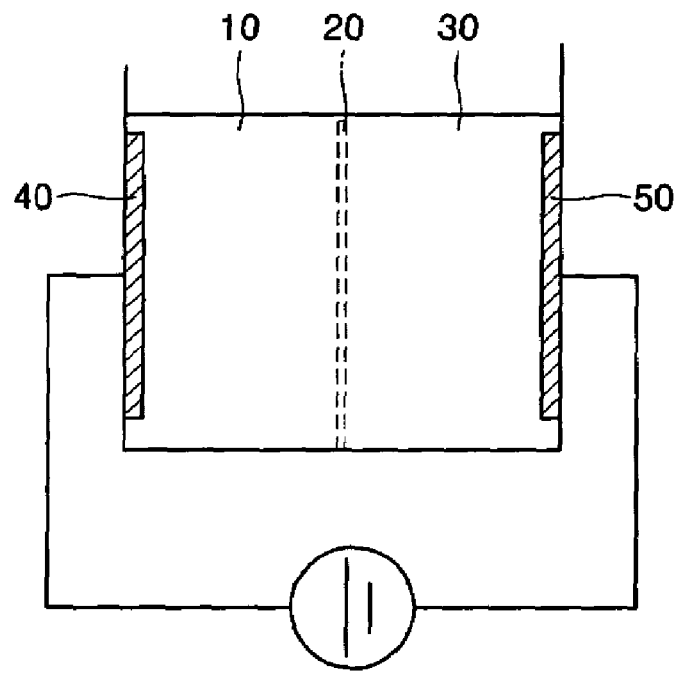
FIG. 1A is a diagram of an electrolysis device having a cathode chamber, an anode chamber, and a separator installed between the cathode chamber and the anode chamber.

The present invention provides a microfluidic device including an electrolysis device for cell lysis which includes an anode chamber, a cathode chamber and a separator, in which the separator is installed between the anode chamber and the cathode chamber, the anode chamber includes an inlet and an outlet for an anode chamber solution and an electrode, and the cathode chamber includes an inlet and an outlet for a cathode chamber solution and an electrode.

The microfluidic device of the present embodiment includes an electrolysis device for cell lysis including an anode chamber, a cathode chamber and a separator. In the electrolysis device for cell lysis, the separator is installed between the anode chamber and the cathode chamber, the anode chamber includes an inlet and an outlet for an anode chamber solution and an electrode, and the cathode chamber includes an inlet and an outlet for a cathode chamber solution and an electrode. The inlet and the outlet do not need to be separated and one port can also act as both the inlet and the outlet.

The electrolysis device for cell lysis included in the microfluidic device of the present embodiment can be used to lyse cells by applying current to electrodes included in each chamber when a solution containing cells or viruses is introduced into the cathode chamber and a proper electrolyte is included in the anode chamber. It is assumed that the cell lysis is achieved due to hydroxide ions generated in the cathode chamber by applying current, but the present invention is not limited to a specific mechanism.

The electrolysis device for cell lysis forms a part of the microfluidic device. For example, the respective inlets and outlets of the anode chamber and the cathode chamber form microchannels of the microfluidic device, and the anode chamber and the cathode chamber form a reactor in the form of a microchannel. In the microfluidic device of the present embodiment, the respective inlets of the anode chamber and the cathode chamber are composed of separate microchannels. In addition, the respective outlets of the anode chamber and the cathode chamber may be separate microchannels or be joined/merged each other. Preferably, the respective outlets of the anode chamber and the cathode chamber are joined/merged so as to mix and neutralize the anode chamber solution and the cathode chamber solution in one microchannel. When forming one joined microchannel, the cell lysate of the cathode chamber can be neutralized without the addition of a separate neutralization solution.

In an embodiment of the present invention, the anode chamber solution may include a compound having lower standard oxidation potential than water. Examples of the compound include anions such as $NO_3^-$, $F^-$, $SO_4^{2-}$, $PO_4^{3-}$ and $CO_3^{2-}$, but are not limited thereto. When the anode chamber solution is a compound having lower standard oxidation potential than water, when electrolysis is performed using the microfluidic device of the present embodiment, water is electrolyzed to produce oxygen gas and $H^+$ ions in the anode chamber.

However, when the anode chamber solution and the cathode chamber solution are mixed and only cell lysis is required without neutralization, the anode chamber solution may include a compound, i.e., an electrolyte, having lower or higher standard oxidation reduction potential than water. Examples of such a compound include anions such as $Cl^-$, $NO^{3-}$, $F^-$, $SO_4^{2-}$, $PO_4^{3-}$, and $CO_3^{2-}$, but are not limited thereto.

In another embodiment of the present invention, the cathode chamber solution may include a compound having lower standard reduction potential than water. Examples of the compound include cations such as $Na^+$, $K^+$, $Ca^{2+}$, $Mg^{2+}$ and $Al^{3+}$, but are not limited thereto. Thus, when electrolysis is performed using the microfluidic device of the present embodiment, water is electrolyzed to produce hydrogen gas and $OH^-$ ions in the cathode chamber.

In the present embodiment, the separator preferably allows current to pass through, but dose not allow ions and/or gas generated from electrolysis of the electrolyte contained in the anode chamber and the cathode chamber to pass through. More preferably, the separator allows electricity to pass through, but does not allow hydrogen ions and hydroxide ions and/or gas to pass through. Examples of the separator include Nafion™ (Dupont), Dowex™ (Aldrich) and Diaion™ (Aldrich), but are not limited thereto.

Electrodes included in the anode chamber and the cathode chamber may be selected from the group consisting of Pt, Au, Cu and Pd. When a Pt electrode is used in the anode chamber, adsorption of proteins and DNA can be prevented. When a Cu electrode is used, it reacts with chloride, such as NaCl, in the anode chamber to form $CuCl_2$, thereby reducing generation of toxic chlorine gas. When a Pd electrode is used, it absorbs hydrogen gas generated in the cathode chamber, and thus a gas removal process is not required.

The microfluidic device of the present embodiment may further include a pump for introducing or discharging a solution to or from the anode chamber and a pump for introducing or discharging a solution to or from the cathode chamber. Alternatively, the microfluidic device may further include a pump for introducing or discharging solutions to or from the anode chamber and the cathode chamber. In this case, solutions of the anode chamber and the cathode chamber are injected using one pump and mixed.

In an embodiment of the present invention, the microfluidic device may include a cell lysis compartment having the above-described electrolysis device for cell lysis, a nucleic acid isolation compartment, a nucleic acid amplification compartment and a detection compartment. The microfluidic device of the present embodiment can act as a LOC. Elements available for the nucleic acid isolation, nucleic acid amplification and detection compartments may be any means known in the art.

The present invention also provides a method of lysing cells or viruses using electrolysis with a microfluidic device including an electrolysis device for cell lysis which includes an anode chamber, a cathode chamber and a separator, in which the separator is installed between the anode chamber and the cathode chamber, the anode chamber includes an inlet and an outlet for an anode chamber solution and an electrode, and the cathode chamber includes an inlet and an outlet for a cathode chamber solution and an electrode, the method including: introducing the anode chamber solution including a compound having lower or higher standard oxidation potential than water into the anode chamber through the inlet of the anode chamber; introducing the cathode chamber solution including cells or viruses and a compound having lower standard reduction potential than water into the cathode chamber through the inlet of the cathode chamber; and lysing cells by applying current to electrodes included in the anode chamber and the cathode chamber to cause electrolysis in the anode chamber and the cathode chamber.

The cell or virus lysis method of the present embodiment includes introducing the anode chamber solution including a compound having lower or higher standard oxidation potential than water into the anode chamber through the inlet of the anode chamber; and introducing the cathode chamber solution including cells or viruses and a compound having lower standard reduction potential than water into the cathode chamber through the inlet of the cathode chamber.

In an embodiment of the present invention, the compound having lower standard oxidation potential than water may be at least one anion among $NO_3^-$, $F^-$, $SO_4^{2-}$, $PO_4^{3-}$ and $CO_3^{2-}$, and the compound having higher standard oxidation potential than water may include $Cl^-$ ion, but is not limited thereto. The compound having lower standard reduction potential than water may be at least one cation among $Na^+$, $K^+$, $Ca^{2+}$, $Mg^{2+}$ and $Al^{3+}$, but is not limited thereto. The two steps can be simultaneously or subsequently performed.

When electrolysis is performed after introducing a sample solution containing NaCl, which is most generally contained in biological sample solutions, into the anode chamber and the cathode chamber, chloride rather than water in the anode chamber are electrolyzed to generate chlorine gas, and thus a smaller amount of hydrogen ion than the amount of hydroxide ion generated in the cathode chamber is generated. The hydrogen ion is generated due to the reaction between chlorine gas and water and its amount varies according to the condition of dissolving chlorine gas, which makes pH control difficult. To solve this problem, in an embodiment of the present invention, the compound having lower standard oxidation potential than water and the compound having lower standard reduction potential than water are used in the anode chamber and the cathode chamber, respectively.

The cell or virus lysis method of the present embodiment includes lysing cells by applying current to electrodes included in the anode chamber and the cathode chamber to cause electrolysis in the anode chamber and the cathode chamber. In the method of the present embodiment, since the cathode chamber contains the cathode chamber solution including the compound having lower standard reduction potential than water, water is electrolyzed to generate hydrogen gas and $OH^-$ ions. Thus, cells or viruses in the cathode chamber can be lysed by hydroxide ions. In addition, in an embodiment of the present invention, since the anode chamber contains the anode chamber solution including the compound having lower standard oxidation potential than water, water is electrolyzed to generate oxygen gas and hydrogen ions. Consequently, the cathode chamber solution turns alkaline and the anode chamber solution turns acidic.

Generally, cell lysates undergo various additional biological analysis processes, such as PCR, nucleic acid isolation or protein isolation. Such biological analysis processes are carried out in a neutral state since biological molecules, such as nucleic acids or proteins, are generally stable in the neutral state. In particular, cell lysis, nucleic acid isolation, nucleic acid amplification, protein isolation and detection can be successively carried out. In this case, cell lysis which is carried out in a relatively early stage should not include a material that can influence on the reaction undergone in the subsequent step. For example, when nucleic acids are amplified using PCR after cell lysis, a material that can inhibit the PCR should not be included.

Thus, the method of the present embodiment further includes, after electrolysis, discharging an acid solution from the anode chamber through the outlet; discharging an alkaline cell or virus lysate from the cathode chamber through the outlet; and mixing the acid solution and the alkaline cell or virus lysate so as to neutralize the cell or virus lysate.

Further, in an embodiment of the present invention, the acid solution from the anode chamber and the alkaline cell or virus lysate from the cathode chamber are neutralized by mixing in a 1:1 volumetric ratio. In the method of the present embodiment, since the hydroxide ion and the hydrogen ion are generated in the cathode chamber solution and the anode chamber solution, respectively, in the same equivalent ratio, even when the cathode chamber solution and the anode chamber solution are mixed in a 1:1 ratio after cell lysis, neutral pH or approximately neutral pH can be obtained.

The microfluidic device used in the method of the present embodiment may further include a pump for introducing or discharging a solution into or from the anode chamber and a pump for introducing or discharging a solution into or from the cathode chamber. Alternatively, the microfluidic device may further include a pump for introducing or discharging solutions into or from the anode chamber and the cathode chamber. In this case, solutions of the anode chamber and the cathode chamber are injected using one pump and mixed.

In addition, the separator included in the electrolysis device for cell lysis of the microfluidic device used in the method of the present embodiment preferably allows current to pass through, but dose not allow ions and/or gas generated by electrolysis of the electrolyte contained in the anode chamber and the cathode chamber to pass through. More preferably, the separator allows electricity to pass through, but does not allow hydrogen ions and hydroxide ions and/or gas to pass through. Examples of the separator include Nafion™ (Dupont), Dowex™ (Aldrich) and Diaion™ (Aldrich), but are not limited thereto.

Electrodes included in the anode chamber and the cathode chamber of the electrolysis device for cell lysis may be selected from the group consisting of Pt, Au, Cu and Pd. When a Pt electrode is used in the anode chamber, adsorption of proteins and DNA can be prevented. When a Cu electrode is used, it reacts with chloride, such as NaCl, in the anode chamber to form $CuCl_2$, thereby reducing generation of toxic chlorine gas. When a Pd electrode is used, it absorbs hydrogen gas generated in the cathode chamber, and thus a gas removal process is not required.

The microfluidic device used in the method of the present embodiment may include a cell lysis compartment having the above-described electrolysis device for cell lysis, a nucleic acid isolation compartment, a nucleic acid amplification compartment and a detection compartment. The microfluidic device can act as a LOC. Elements available for the nucleic acid isolation, nucleic acid amplification and detection compartments may be any means known in the art.

FIG. 1A is a schematic diagram of an electrolysis device used in the microfluidic device according to an embodiment of the present invention. Referring to FIG. 1A, a cathode chamber 10 and an anode chamber 30 are separated by a separator 20. An electrode 40 and an electrode 50 are installed in the respective chambers, and thus electrolysis in each chamber can be caused by applying voltage to each electrode. In FIG. 1A, an inlet and an outlet for a chamber solution are integrated and can be embodied by opening and closing the upper lid.

Figure 1B:
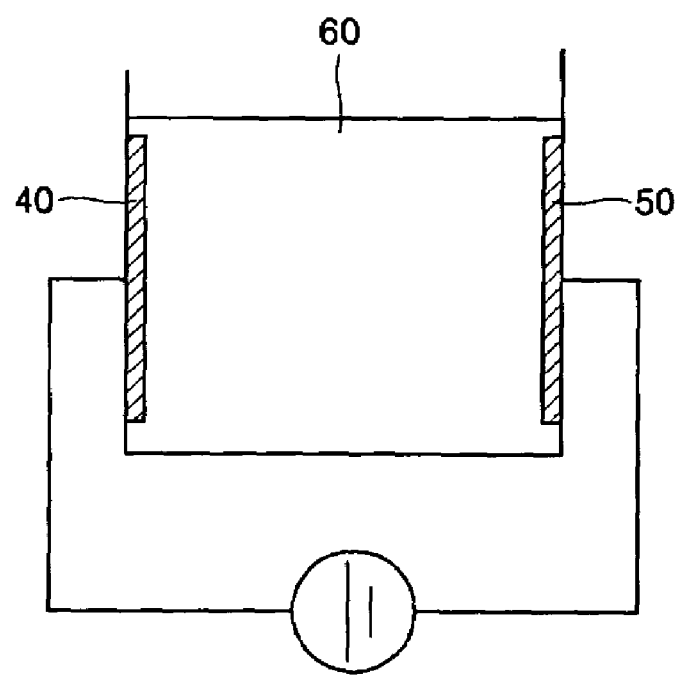
FIG. 1B is a diagram of an electrolysis device including a cathode chamber and an anode chamber, used as a control electrolysis device in Example 1 of the present invention.
Figure 1C:
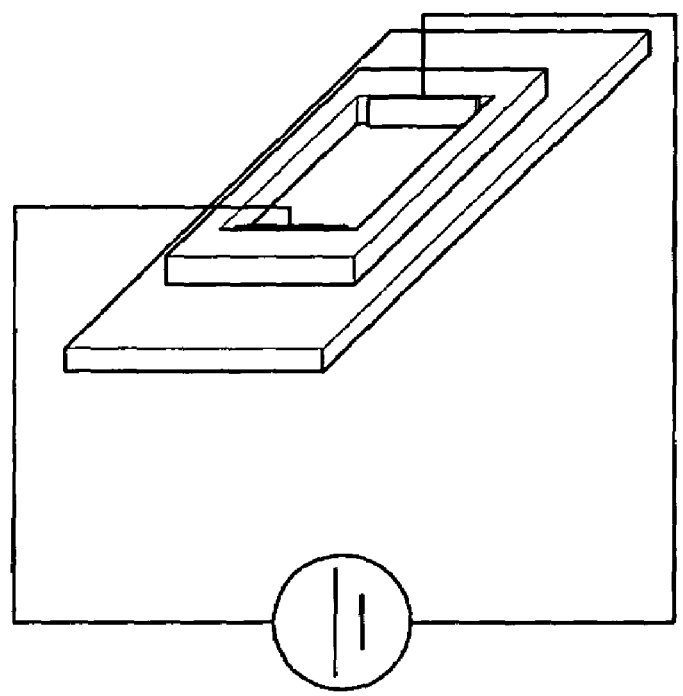
FIG. 1C is a diagram of an electrolysis device including a cathode chamber and an anode chamber, implemented on a slide glass for microscopic observation, used as a control electrolysis device in Example 1 of the present invention.
Figure 1D:
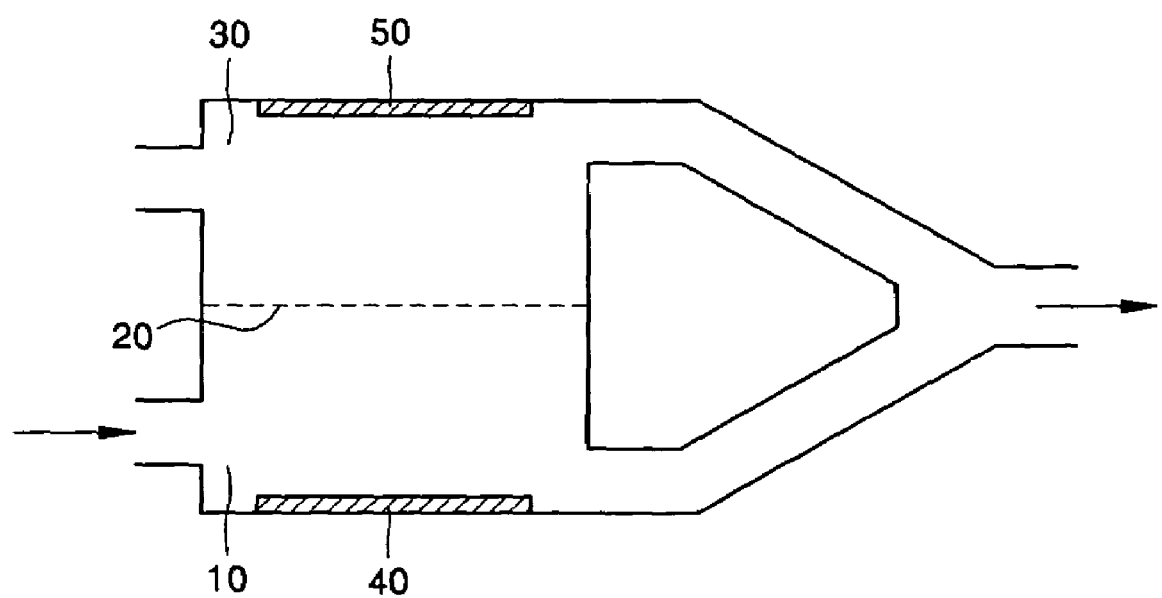
FIG. 1D is a diagram of a microfluidic device including an electrolysis device according to an embodiment of the present invention.

FIG. 1D is a schematic diagram of a microfluidic device including the electrolysis device according to an embodiment of the present invention. Referring to FIG. 1D, a cathode chamber 10 and an anode chamber 30 are separated by a separator 20. An electrode 40 and an electrode 50 are installed in the respective chambers, and thus electrolysis in each chamber can be caused by applying voltage to each electrode. An inlet and an outlet are formed in each chamber and outlets are joined so as to mix solutions electrolyzed in the anode chamber and the cathode chamber.

Figure 1E:
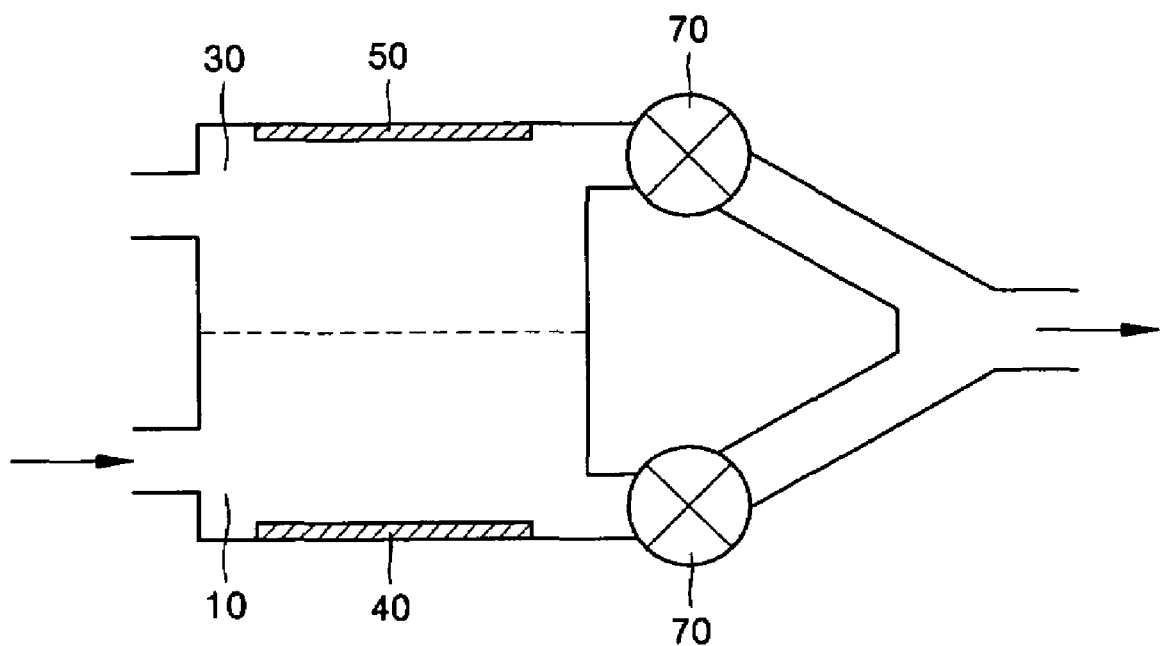
FIGS. 1E and 1F are diagrams of microfluidic devices including an electrolysis device according to another embodiments of the present invention, in which two pumps and one pump, respectively, are installed.
Figure 1F:
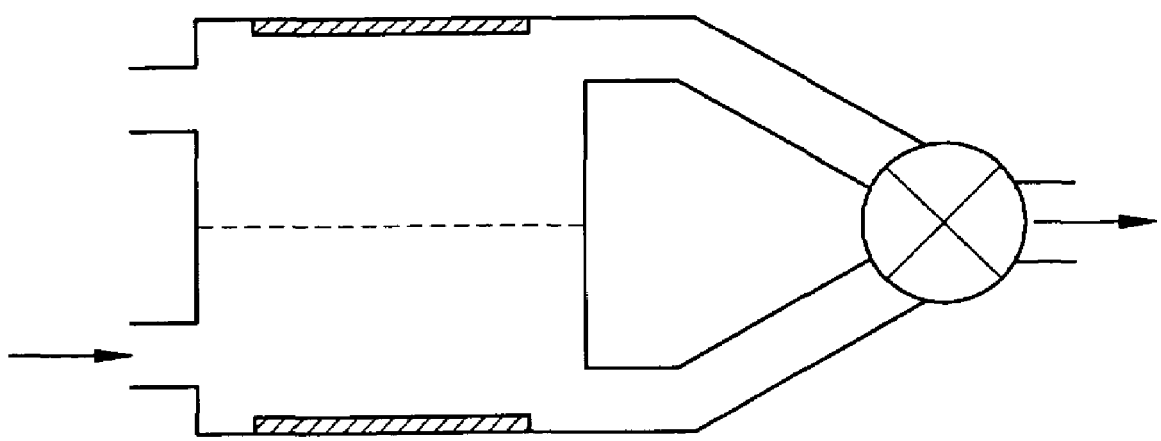

FIGS. 1E and 1F are schematic diagrams of another microfluidic devices including an electrolysis device according to an embodiment of the present invention. Microfluidic devices illustrated in FIGS. 1E and 1F are the same as the microfluidic device illustrated in FIG. 1D, except that they further include two micropumps 70 and one micropump, respectively. In the microfluidic device having a micropump as illustrated in FIG. 1F, electrolyzed solutions of the anode chamber and the cathode chamber are injected in the same amounts to be mixed, and thus this embodiment is possible only when the equivalent of hydrogen ion generated in the anode chamber and the equivalent of hydroxide ion generated in the cathode chamber through electrolysis are similar to each other.

The present invention will now be described in greater detail with reference to the following examples. The following examples are for illustrative purposes only and are not intended to limit the scope of the invention.

EXAMPLES

Example 1

Cell Lysis Through Electrolyzed Solutions of a Cathode Chamber and an Anode Chamber In the present Example, cell lysis was caused using a cathode chamber solution and an anode chamber solution obtained after performing electrolysis using an electrolysis device having a cathode chamber, an anode chamber, and a separator installed between the cathode chamber and the anode chamber, and the results were observed.

The electrolysis device used in the present Example is illustrated in FIG. 1A. Referring to FIG. 1A, the electrolysis device includes a cathode chamber, an anode chamber, and a separator installed between the cathode chamber and the anode chamber. A Au electrode and a Pt electrode were included in the cathode chamber and the anode chamber, respectively, and the cathode chamber and the anode chamber were separated by a Nafion™ membrane (Dupont, USA).

(1) Preparation of Electrolyzed Solutions

Electrolysis was caused by adding 300 mL of 100 mM NaCl aqueous solution to the cathode chamber and the anode chamber and applying a DC voltage of 10 V at room temperature for 5 minutes. As a result, an electrolyzed acid solution (EAS) was obtained from the anode chamber, an electrolyzed alkaline solution (EBS) was obtained from the cathode chamber, and an electrolyzed total solution (ETS) was obtained by mixing the EAS and the EBS in equal volumes. These solutions were used to carry out cell lysis. The pH of each solution was measured using a pH sensor (AR15, Fisher scientific, USA).

(2) Cell Lysis Using Electrolyzed Solutions

*E. coli* (ATCC #45020) was cultured in 100 mL of LB medium in a flask while stirring at 37° C. and 250 rpm for 6 to 8 hours. Cells were collected using an Eppendorf 5810R centrifuge at 4° C. and 6,000 g for 10 min. The *E. coli* was suspended in a phosphate buffered saline (PBS) to the concentration of *E. coli* cell, $OD_{600}$ value, of 0.8. The cell suspension was treated with the electrolyzed solutions, i.e. EAS, EBS and ETS, respectively, at room temperature for 5 minutes. After reaction, samples were spin downed using the Eppendorf 5810R centrifuge (Eppendorf AG, Germany) at 4° C. and 10,000 g for 10 min. As a result, a supernatant and a subnatant of the obtained sample were used for analysis.

(3) Identification of Cell Lysis Through Realtime PCR

To identify the occurrence of cell lysis, a realtime PCR was performed using the supernatant and the subnatant of the sample as templates. The occurrence of cell lysis was indirectly presumed from the results. PCR target sequence was a part of core domain of HBV genome recombinated into *E. coli* genome.

PCR was performed using the supernatant and the subnatant as templates and oligonucleotides of SEQ ID No:1 and SEQ ID No:2 as primers and using LightCycler instrument (Roche Diagnostics, Germany) in a reaction volume of 20 μl. For LightCycler PCR reaction, a reaction mastermix of the following reaction components was prepared to the indicated final concentration: 2 μl LightCycler master (Fast start DNA master SYBR Green I; Roche Diagnostics), 3.2 μl $MgCl_2$ (5 mM), 1.0 μl forward-reverse primer mix (1.0 mM), 4.0 μl UNG (Uracil-N-Glycosylase, 0.2 unit) and 4.8 μl PCR-grade water. 5 μl of a sample to be tested was added to the mastermix. Two different Taq DNA polymerases (Roche Hot-start Taq DNA polymerase and Solgent Taq DNA polymerase) were used to prepare the LightCycler master.

Then, 20 μl of the reaction mixture was dispensed in a lightCycler capillary. The capillary was closed and located on a lightCycler rotor. The following two LightCycler protocols were used for two different enzymes: (1) for Hot-start Taq DNA polymerase (Roche Diagnostics), UNG effect program (10 min at 50° C.); initial denaturation (10 min at 95° C.); 35 amplification and quantification cycles (5 sec at 95° C.; 15 sec at 62° C., and once fluorescence detection); melting curve program (continuous fluorescence detection and ramping rate of 1° C./sec at 62-95° C.); and final cooling to 40° C. and (2) for Taq DNA polymerase (Solgent), UNG effect program (10 min at 50° C.); initial denaturation (1 min at 95° C.); 35 amplification and quantification cycles (5 sec at 95° C.; 15 sec at 62° C., with once fluorescence detection); melting curve program (continuous fluorescence detection and ramping rate of 1° C./sec at 62-95° C.); and final cooling to 40° C.

(4) Analysis of the Amplified Product

For visualization, 1 μl of the amplified product was assayed with Agilent 2100 Bioanalyzer system. DNA 500 Labchips (Agilent Technologies, USA) were used to detect the percentage of the PCR product and dimer. To be briefly, 9 μl of a gel-dye mixture was pipeted to a proper well, and then the well was pressurized through a 1 mL syringe for 1 min to filling a microchannel with the mixture. Then, a ladder well and a sample well were loaded with 5 μl of a DNA size marker mixture+1 μl of a molecular size ladder or sample. Immediately after mixing by means of vortexing, chips were inserted into the bioanalyzer system and treated according to manufacturer's guideline. The amount of the PCR product was determined by a relative area ratio of two peaks of a dimer and a wild DNA fragment.

(5) Results

Effects of electrolyzed solutions on lysis of E. coli cells were investigated. As control groups, a boiled sample and an untreated sample were used. The boiling treatment was carried out at 95° C. for 5 min and the untreated sample was suspended in PBS (pH 7). The cell suspension was treated with three types of electrolyzed solution prepared above. The treated cells were collected and overnight cultured on the LB agar plate. Then, the occurrence of cell lysis was observed.

Figure 2:
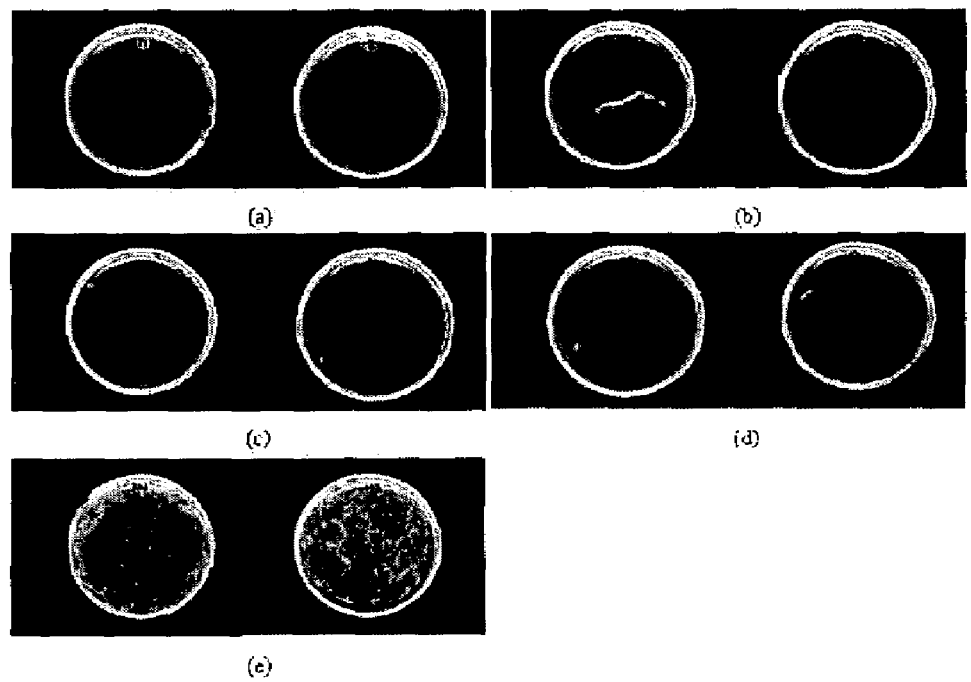
FIG. 2 illustrates agar plates after culturing cells treated with a solution obtained by electrolysis at 37° C. for 16 hours.

FIG. 2 illustrates agar plates after culturing cells at 37° C. for 16 hours. Referring to FIG. 2, while the EAS, the EBS, the ETS and the boiled sample in petridishes (a), (b), (c) and (d), respectively, were not grown, the untreated sample (control) in a petridish (e) grew. No colony could be observed in the electrolyzed solutions and the boiled cell, indicating that E. coli lost viability due to all electrolyzed solutions and boiling. However, it was not certain whether all cells were disrupted, which was identified through the following realtime PCR.

Figure 3:
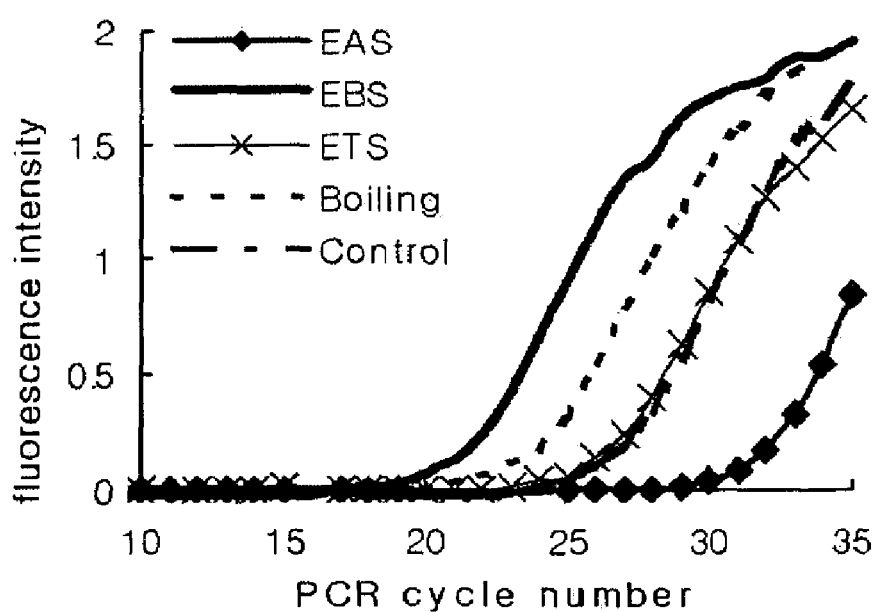
FIG. 3 illustrates a realtime PCR curve obtained by a realtime PCR performed using a solution which is obtained by treating cells with an electrolyzed solution as a template.

To identify whether cells were disrupted, a realtime PCR was performed. If cell membrane was lysed, gene originated from cell can be analysed by the realtime PCR. To ensure accuracy and reproduction of the realtime PCR, variation in analysis was determined by three repetitions within LightCycler development. The realtime PCR curve was used to quantify gene originated from the disrupted cell. FIG. 3 is a realtime PCR curve obtained when performing the realtime PCR in which solutions obtained by treating cells with electrolyzed solutions were used as templates. These curves illustrates the number of initial template copying which was plotted in a longitudinal axis and the number of cycles in crossing point which was plotted in a horizontal axis by measuring the amount of the amplified DNA. The amount of DNA with respect to the number of cycles had a shape of log as illustrated in FIG. 3. A threshold cycle number Ct is a point at which the log line cuts the horizontal threshold line. The amount of target is equal in all samples at Ct of crossing point. That is, if the number of cycles at which the amount of target reached a certain level was small, it indicated that the amount of initial DNA is large, and if the number of cycles was large, it indicated that the amount of initial DNA is small. The amplification procedure of log phase is expressed by the following equation:

$$Ct=-(1/\log E)\log T0+(\log K/\log E).$$

In the equation, T0 is the initial amount of target, K is the crossing point, and E is the efficiency of amplification. Ct is the measured value and T0 is a standard initial concentration determined by experimenters. The inventors presumed the concentration of nucleic acid derived from the disrupted cells with the Ct value. Comparing the results of five cell lysis methods, significant differences were observed. Based on Ct value, the amount of nucleic acid was increased in the following order: EBS treated cell>boiled cell>ETS treated cell>control>EAS treated cell (see Table 1).

TABLE 1

Ct values of undiluted sample and 1/10 diluted suspension in PBS

| Treatment | Undiluted suspension | 1/10 diluted suspension |
| --- | --- | --- |
| EAS | — | — |
| EBS | 20.21 ± 0.10 | 26.19 ± 0.05 |
| ETS | 25.18 ± 0.16 | — |
| Boiling | 22.79 ± 0.25 | 26.78 ± 0.48 |
| Control | 25.68 ± 0.27 | — |

In Table 1, "—" indicates no Ct value and control indicates an untreated sample.

As represented in Table 1, the undiluted sample treated with EBS had higher initial concentration of nucleic acid than boiled sample. These data showed that among tested methods, EBS treatment was most effective cell lysis method.

Moreover, Labchip proved specificity of the amplified PCR product. In addition, the concentration of PCR product of the EBS treated sample was higher than other samples, which also indicates that EBS treatment is more effective than boiling treatment, which is usually used.

Figure 4:
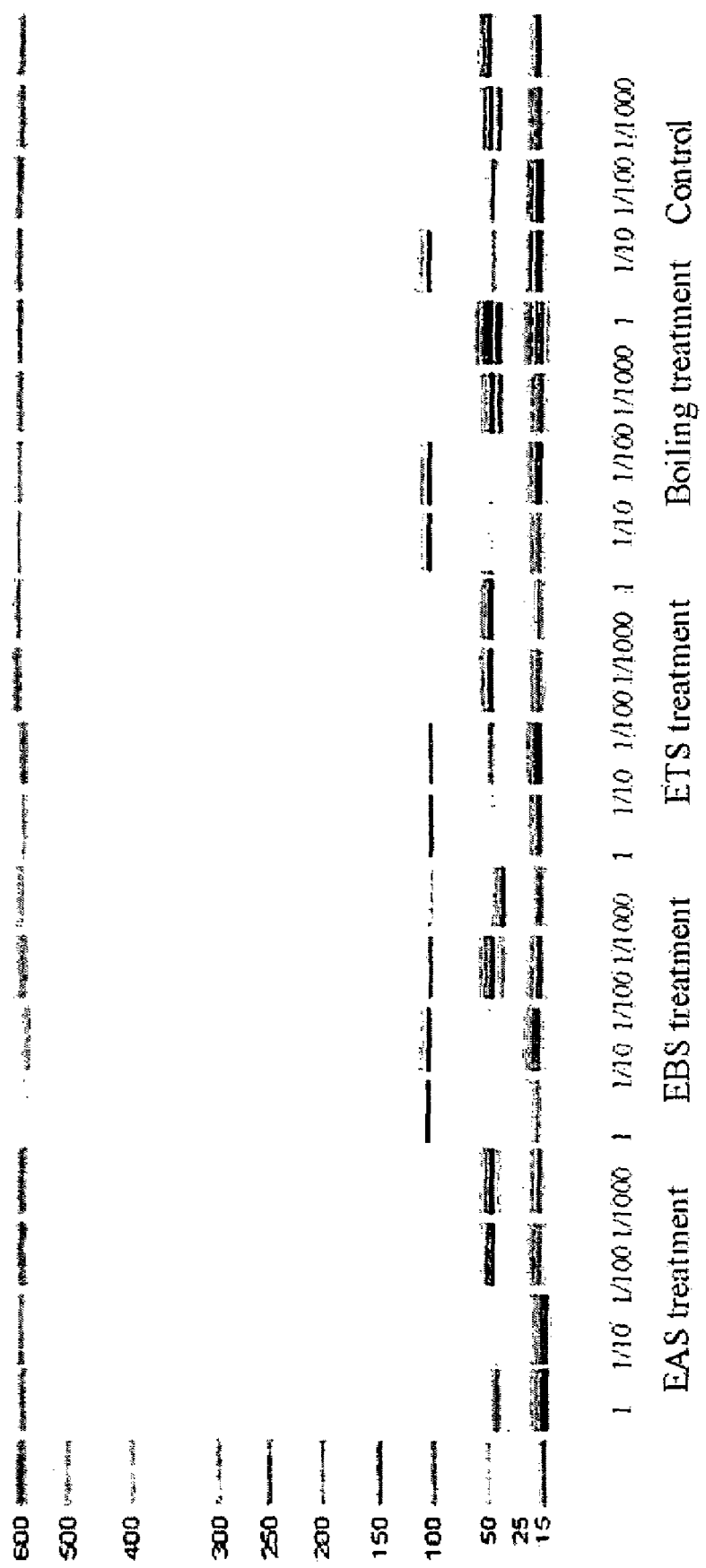
FIG. 4 is a diagram of analyzing with Agilent 2100 Bioanalyzer after electrophoresis of PCR products obtained by performing a realtime PCR using a solution which is obtained by treating cells with an electrolyzed solution as a template.
Figure 5:
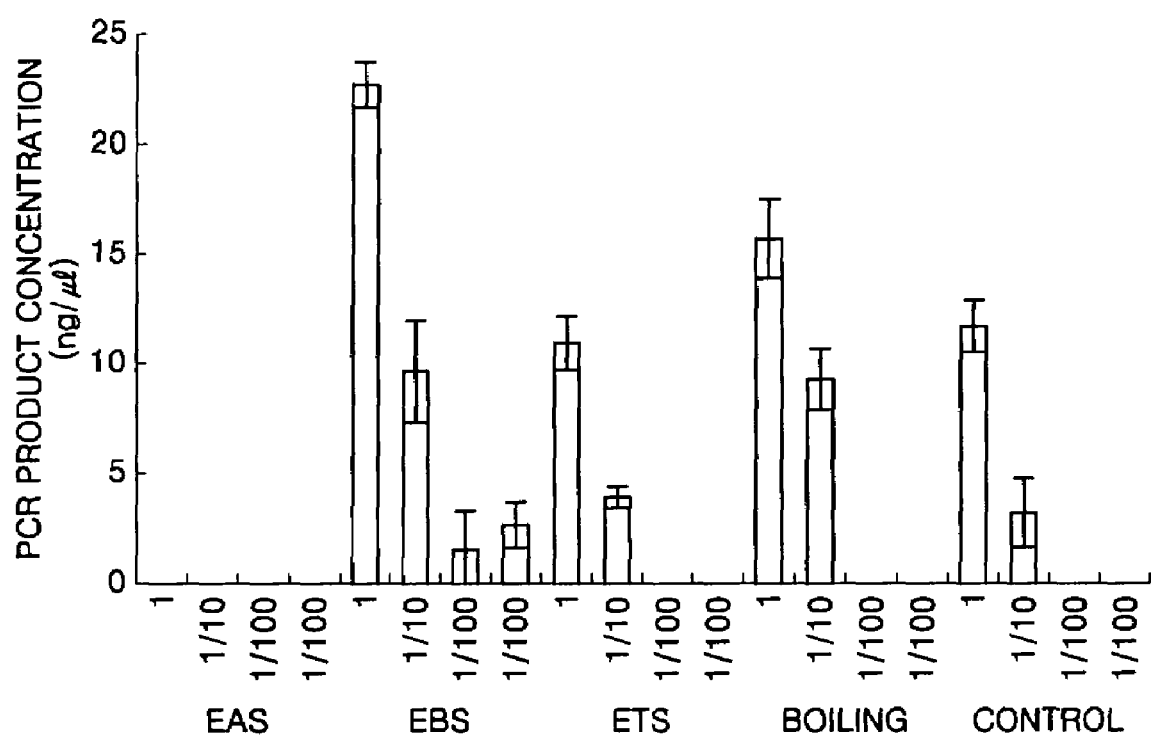
FIG. 5 is a graph illustrating the results of FIG. 4 as concentrations of PCR products.

FIG. 4 illustrates the results of analysing the PCR product obtained by performing a realtime PCR, in which solutions obtained by treating cells with electrolyzed solutions were used as templates, with Agilent 2100 Bioanalyzer after electrophoresis. In FIG. 4, the boiling treatment is carried out at 95° C. for 5 min. Referring to FIG. 4, PCR products from the EAS treated cell were all dimers, indicating that PCR was not well performed. While PCR products were not observed in all EAS treated samples, PCR products were observed in the undiluted sample and the 1/10 diluted sample as control samples. It is assumed that PCR products are not observed in the EAS treated sample since EAS includes a PCR inhibitor. Thus, the concentration of PCR product of the sample treated with ETS containing EAS was lower than that of EBS treated sample (see FIG. 5). FIG. 5 is a graph illustrating the results of FIG. 4 as the concentration of PCR product.

It was identified from the above results that for biological analysis such as PCR, treatment with EBS produced in a cathode chamber is most efficient to lyse cells, and biological analysis such as PCR can effectively achieved.

Example 2

Direct Cell Lysis in an Electrolysis Chamber

In the present Example, cells was injected into a chamber for electrolysis and an electrolyzed solution was in situ produced, followed by determining cell lysis efficiency.

(1) Device for Electrolysis

Electrolysis devices illustrated in FIGS. 1A, 1B and 1C were used. The electrolysis device of FIG. 1A is as described in Example 1. To generate hydroxide ions for cell lysis, 12 mL of 10 mM or 100 mM NaCl solution including *E. coli* was electrolyzed with a DC voltage of 5 V at room temperature for 1 or 3 min.

The electrolysis device of FIG. 1B is the same as the electrolysis device of FIG. 1A, except that a separator separating an anode chamber and a cathode chamber was not included. The distance between electrodes was 2 cm. The electrolysis device of FIG. 1C was the same as the electrolysis device of FIG. 1B, except that it was placed on a slide glass (Corning, USA) so that observation by a digital camera fixed to a microscope was possible. Electrodes were installed at edges of a wall and the distance between electrodes was 4 cm. 500 µl of a CHO cell suspension containing 100 mM NaCl was electrolyzed using these devices by applying a DC voltage of 5 V for 30 sec.

(2) Analysis Method

A cell lysate collected immediately after electrolysis was observed as described in Example 1 through a realtime PCR and analysis of amplified products. Microscopic analysis captured images using Nikon Eclipse TE 300 fluorescence microscope (Nikon, Japan) having a digital camera (Photometrics Inc., USA).

(3) Results

Figure 6:
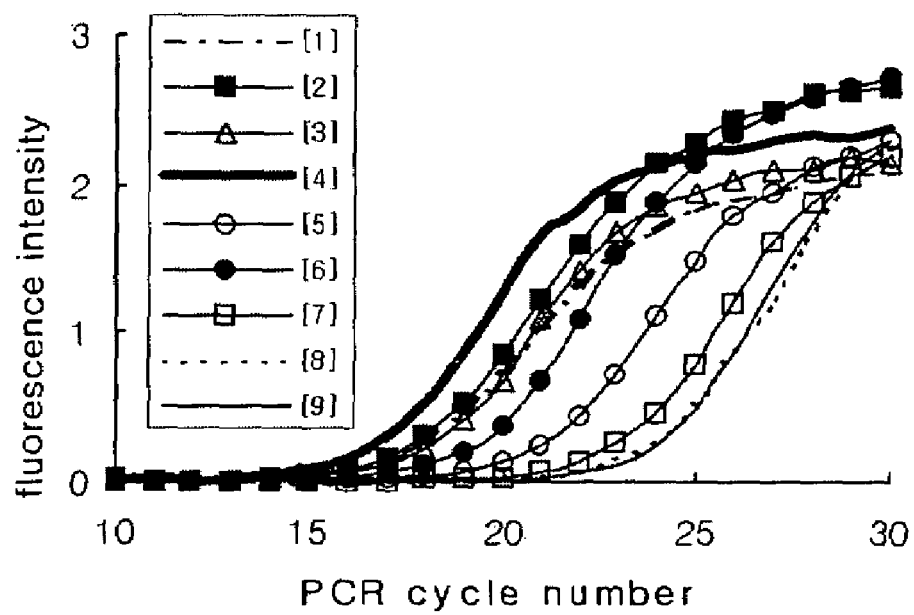
FIG. 6 illustrates the results of a realtime PCR amplification performed using a cell lysate which is obtained by directly electrolyzing a cell solution under conditions of used salt concentration, current and time as a template.

FIG. 6 illustrates the results of realtime PCR amplification performed using cell lysates obtained by electrolysis under conditions of used salt concentration, current and time as templates. In FIG. 6, [1] to [4] were the results obtained using an electrolysis device having a Nafion™ membrane and [5] to [8] were the results obtained using an electrolysis device without membrane. [1] is for electrolysis of 100 mM NaCl solution for 1 min, [2] is for electrolysis of 100 mM NaCl solution for 3 min, [3] is for electrolysis of 10 mM NaCl solution for 1 min, [4] is for electrolysis of 10 mM NaCl solution for 3 min, [5] is for electrolysis of 100 mM NaCl solution for 1 min, [6] is for electrolysis of 100 mM NaCl solution for 3 min, [7] is for electrolysis of 10 mM NaCl solution for 1 min, [8] is for electrolysis of 10 mM NaCl solution for 3 min, and [9] is control.

Table 2 shows Ct values derived from the realtime PCR amplification curve which was obtained using cell lysates obtained by electrolysis under conditions of used salt concentration, current and time as templates.

TABLE 2

| | Ct values under various conditions | | | |
|---|---|---|---|---|
| No. | Membrane | Salt concentration (mM) | Time | Ct |
| [1] | ○ | 100 | 1 | 16.43 ± 0.11 |
| [2] | ○ | 100 | 3 | 16.62 ± 0.12 |
| [3] | ○ | 10 | 1 | 16.70 ± 0.01 |
| [4] | ○ | 10 | 3 | 15.30 ± 0.01 |
| [5] | X | 100 | 1 | 19.74 ± 0.01 |
| [6] | X | 100 | 3 | 18.11 ± 0.02 |
| [7] | X | 10 | 1 | 21.45 ± 0.47 |
| [8] | X | 10 | 3 | 21.29 ± 0.40 |
| [9] | Control | | | 22.86±0.48 |

As shown in Table 2, [4] (with membrane, 10 mM NaCl, applying current for 3 min) represented the strongest signal and the lowest Ct value, indicating that cells were most efficiently lysed under the condition of [4]. This result indicates that in a device having a membrane at the center, cell lysis in EBS is more effective than cell lysis in the mixture of EBS and EAS. Since the Nafion™ membrane prevents mixing of solutions electrolyzed from the anode and the cathode, EAS and EBS were separated in the electrolysis device.

Figure 7:
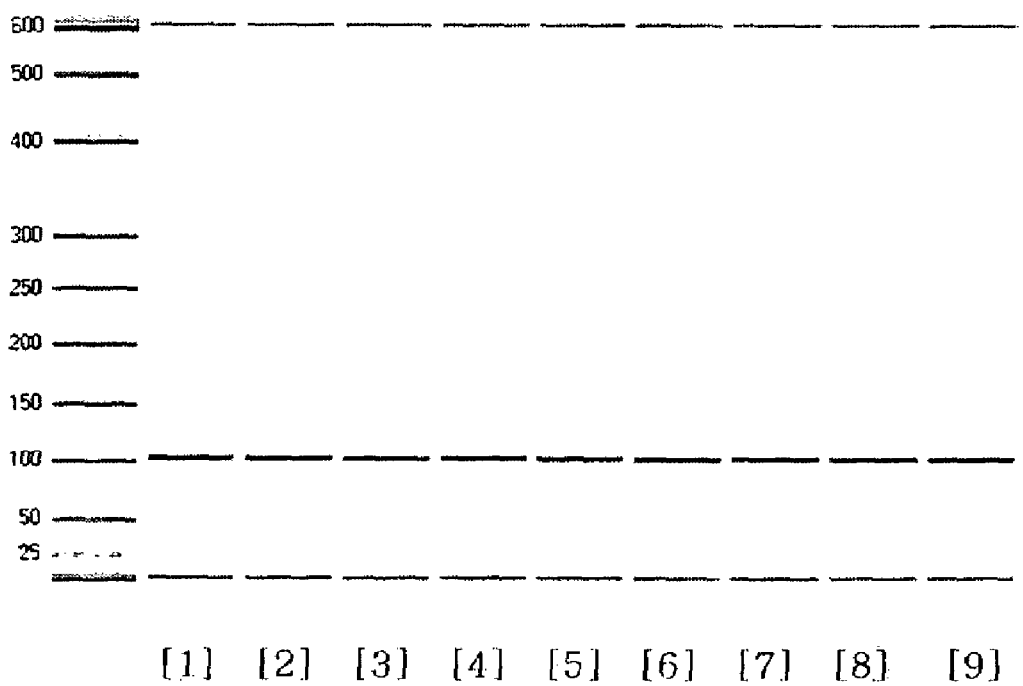
FIG. 7 illustrates the results of electrophoresis of final PCR products obtained by performing PCR using a cell lysate which is obtained by directly electrolyzing a cell solution under various conditions as a template.
Figure 8:
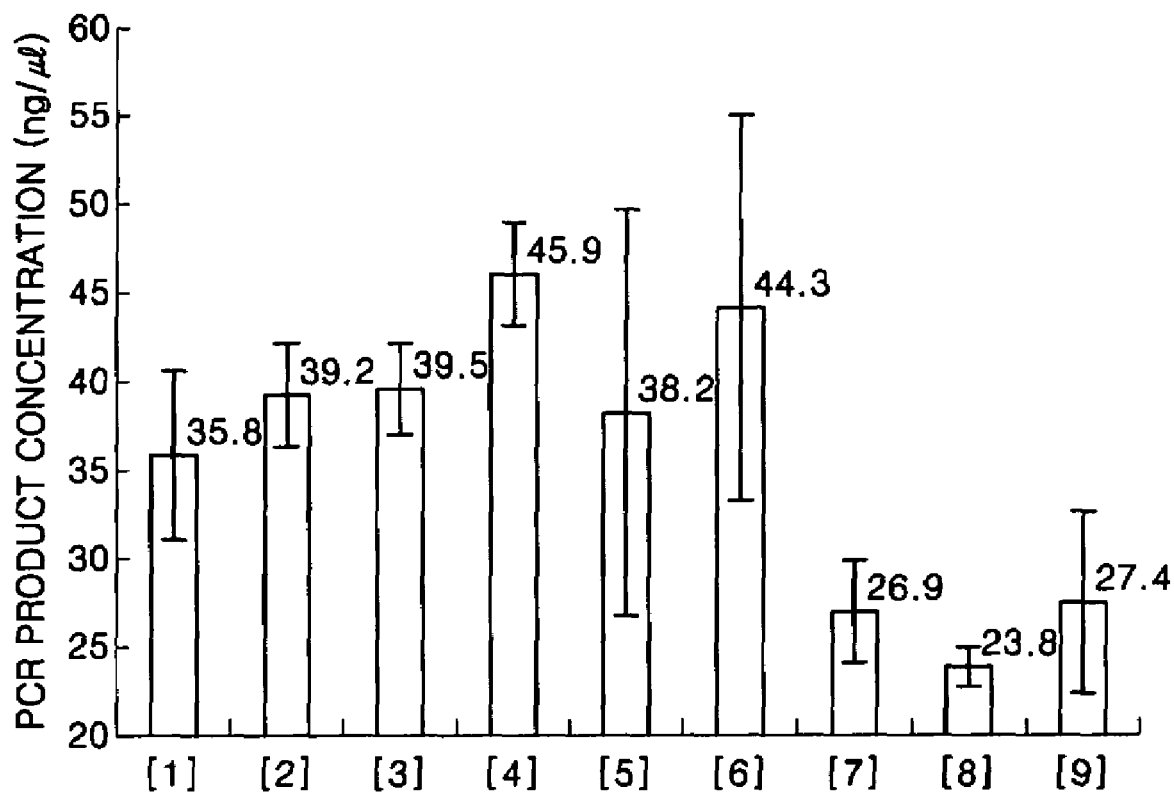
FIG. 8 is a diagram of analyzing the PCR products obtained by performing a realtime PCR using cell lysates obtained by electrolysis in FIG. 6 as templates, with Agilent 2100 Bioanalyzer after electrophoresis.

FIG. 7 illustrates the results of analysing the final PCR product, which is obtained by PCR performed using cell lysates obtained by electrolysis under various conditions as templates, through electrophoresis. As illustrated in FIG. 7, only amplified products without a primer dimer were obtained. FIG. 8 is a diagram of analyzing the PCR products obtained by performing a realtime PCR using cell lysates obtained by electrolysis in FIG. 6 as templates, with Agilent 2100 Bioanalyzer after electrophoresis.

Figure 9:
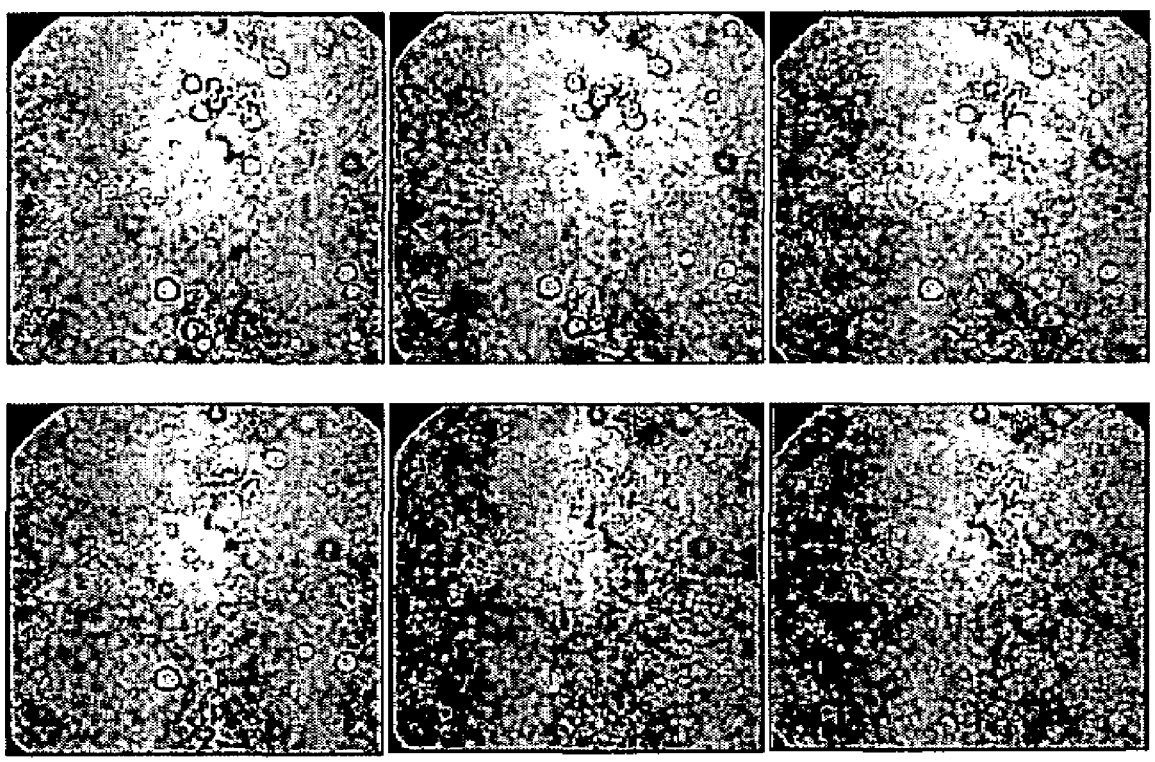
FIG. 9 illustrates the results of continuously observing CHO cells in a well on a slide glass after applying a DC voltage of 5V and a current of 1 mA with a digital camera attached to a microscope.

FIG. 9 illustrates the results of continuously observing CHO cells on a well on the slide glass by applying a DC voltage of 5 V and a current of 1 mA with the digital camera fixed to the microscope. As illustrated in FIG. 9, cells were deformed within very short time and finally disrupted. The results of FIG. 9 demonstrated that hydroxide ions which were electrochemically generated rapidly lysed cells. Cell lysis occurred near the cathode where hydroxide ions were generated.

Example 3

Neutralization of Cell Lysate Obtained by Electrolysis

In the present Example, an electrolysis device having an anode chamber, a cathode chamber and a separator installed between the anode chamber and the cathode chamber as illustrated in FIG. 1A was used and various solutions were electrolyzed in the anode chamber and the cathode chamber, and then the variation in pH of the obtained solutions was observed.

Figure 10:
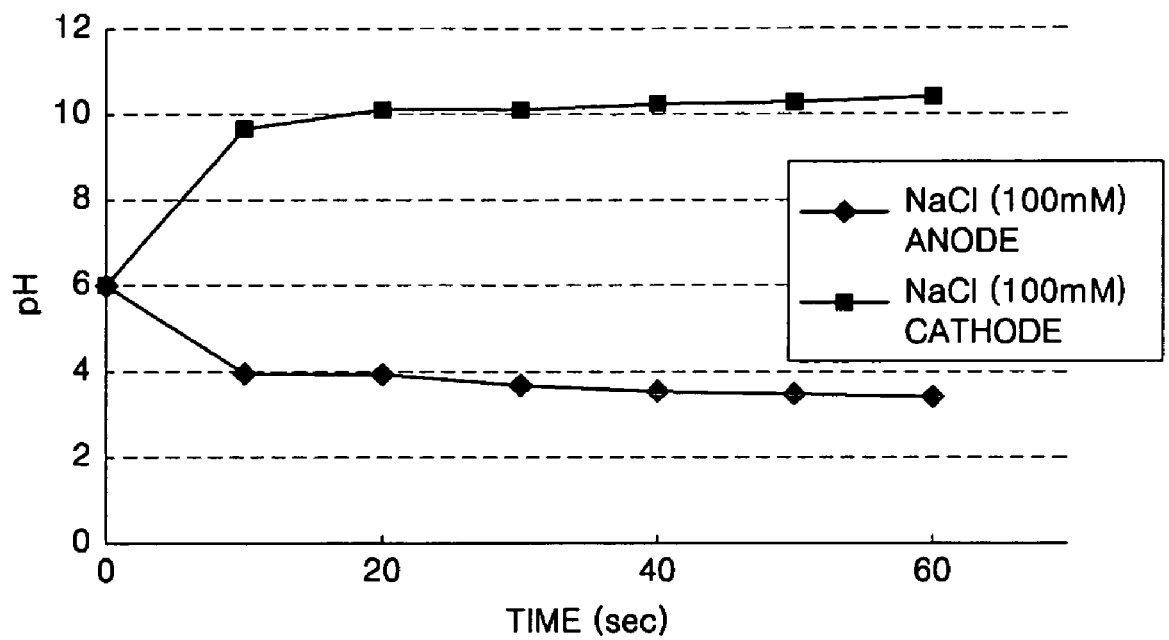
FIG. 10 illustrates the results of observing the variation in pH with time after adding 10 mL of 100 mM NaCl aqueous solution (initial pH=6.0) to each of an anode chamber and a cathode chamber and applying a DC voltage of 5 V.

FIG. 10 illustrates the results of observing the variation in pH with time when adding 10 mL of 100 mM NaCl aqueous solution (initial pH=6.0) to each of the anode chamber and the cathode chamber and applying a DC voltage of 5 V. After 60 sec, the pH of a 1:1 mixture of the anode chamber solution and the cathode chamber solution was 9.49. Thus, it can be seen that when the anode chamber solution and the cathode chamber solution were mixed in a ratio of 1:1, the mixture was not neutralized to initial pH but became alkaline.

Figure 11:
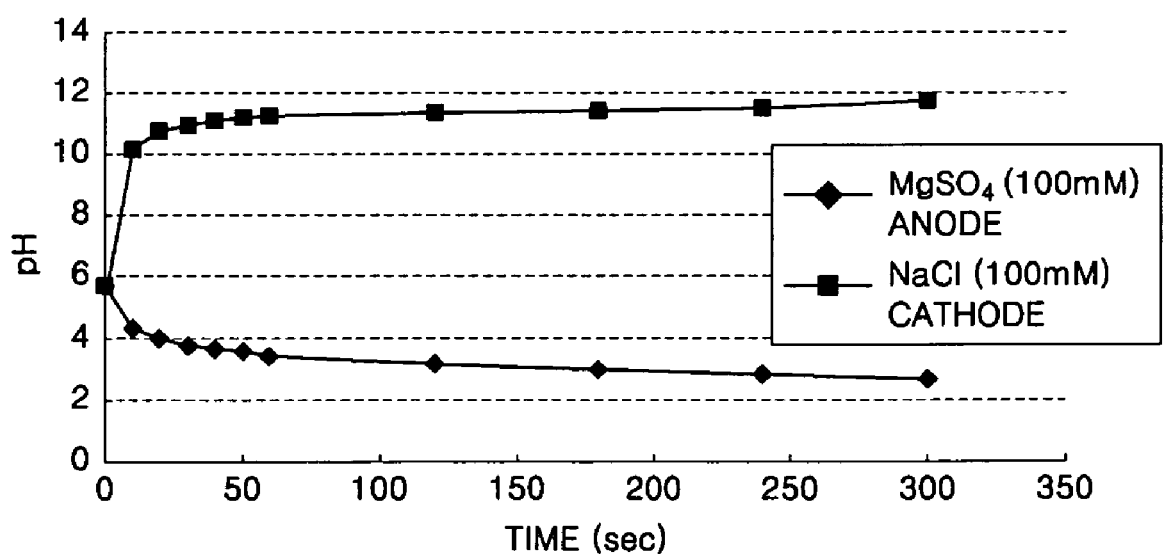
FIG. 11 illustrates the results of observing the variation in pH with time after adding 200 mL of 100 mM $MgSO_4$ aqueous solution (initial pH=5.75) and 200 mL of 100 mM NaCl aqueous solution (initial pH=5.75) to an anode chamber and a cathode chamber, respectively, and applying a DC voltage of 10 V.

FIG. 11 illustrates the results of observing the variation in pH with time when adding 200 mL of 100 mM MgSO$_4$ aqueous solution (initial pH=5.75) and 200 mL of 100 mM NaCl aqueous solution (initial pH=5.75) to the anode chamber and the cathode chamber, respectively, and applying a DC voltage of 10 V. After 300 sec, the pH of a 1:1 mixture of the anode chamber solution and the cathode chamber solution was 5.75, which was the same as the initial pH.

Figure 12:
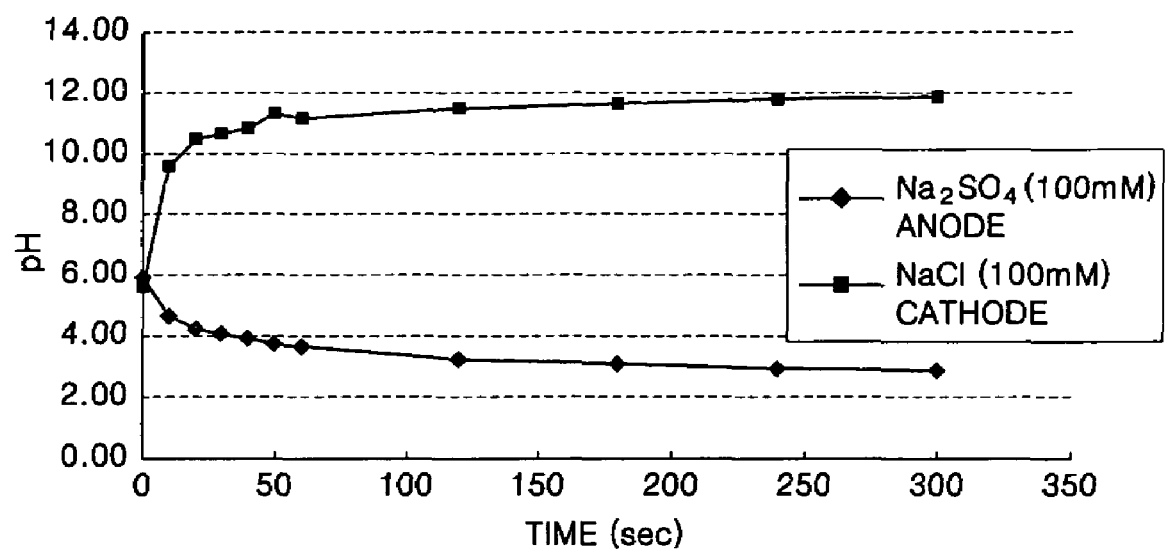
FIG. 12 illustrates the results of observing the variation in pH with time after adding 200 mL of 100 mM $Na_2SO_4$ aqueous solution (initial pH=5.82) and 200 mL of 100 mM NaCl aqueous solution (initial pH=5.82) to an anode chamber and a cathode chamber, respectively, and applying a DC voltage of 10 V.

FIG. 12 illustrates the results of observing the variation in pH with time when adding 200 mL of 100 mM $Na_2SO_4$ aqueous solution (initial pH=5.82) and 200 mL of 100 mM NaCl aqueous solution (initial pH=5.82) to the anode chamber and the cathode chamber, respectively, and applying a DC voltage of 10 V. After 300 sec, the pH of a 1:1 mixture of the anode chamber solution and the cathode chamber solution was 5.82, which was the same as the initial pH.

The results of FIG. 10 can be explained by the reaction theory as described below, but the present invention is not bound to a specific theory.

As shown in the following reaction scheme, water is reduced to generate chlorine in the anode chamber and water is reduced to generate hydrogen gas and hydroxide ions in the cathode chamber during electrolyzing the solution containing NaCl.

Anode Reaction:

$$2Na^+(aq)+2Cl^-(aq)+2H_2O(l) \rightarrow Cl_2(g)+2Na^+(aq) \quad (1)$$

$$2Cl^- \rightarrow Cl_2+2e^-$$

$$Cl_2(aq)+H_2O \rightarrow HOCl(aq)+H^++Cl^-$$

$$HOCl(aq) \rightarrow H^++OCl^-$$

Cathode Reaction:

$$2Na^+(aq)+2Cl^-(aq)+2H_2O(l) \rightarrow H_2(g)+2Na^+(aq)+2OH^-(aq) \quad (2)$$

$$2H_2O+2e^- \rightarrow H_2+2OH^-(aq)$$

Chlorine generated in the anode chamber is properly dissolved in water and reacted with water to generate HOCl and HCl. HOCl generated in the anode chamber disinfects, whereas hydroxide ions generated in the cathode chamber effectively disrupt cells like sodium hydroxide in alkaline cell lysis. That is, HOCl does not disrupt bacteria but kills them, and hydroxide disrupts cells.

In addition, as shown in the above reaction scheme, $H^+$ ions generated in the anode chamber are generated due to $Cl_2$ gas dissolved in water, whereas hydroxide is generated due to reduction of water. As a result, more hydroxide ions than $H^+$ ions are generated. Thus, when the anode chamber solution and the cathode chamber solution, which were obtained by electrolysis, were mixed in a ratio of 1:1, the mixture turned more alkaline than the initial solution.

Meanwhile, as shown in FIGS. 11 and 12, when the anode chamber includes ions having lower standard oxidation potential than water, such as $MgSO_4$ or $Na_2SO_4$, oxygen gas and $2H^+$ ions are generated therein. Also, when a solution including ions with lower standard reduction potential than water, such as $Na^+$ ion, is used in the cathode chamber, water is hydrolysed to generate hydrogen gas and $2OH^-$ ions. Thus, $2H^+$ ions and $2OH^-$ ions are generated in the same equivalents in the anode chamber and the cathode chamber, a neutralized solution can be obtained by mixing the electrolyzed solutions of the respective chambers in a ratio of 1:1.

Since many biological analysis processes have high efficiency at neutral pH, it is particularly preferable that the solution including ions having lower standard oxidation potential than water is used in the anode chamber and the solution including ions with lower standard reduction potential than water is used in the cathode chamber. In this case, as apparent from the above Example, generation of materials, such as HOCl or $Cl^-$ that can potentially inhibit biological processes, such as PCR, can be reduced. Moreover, although two pumps was conventionally required in an electrolysis device in order to obtain a neutralized solution by controlling flow rates of the cathode chamber solution and the anode chamber solution, respectively, only one flow rate control pump may be used in the present invention since the neutralized solution can be obtained just by mixing the solution electrolyzed in the cathode chamber and the solution electrolyzed in the anode chamber (see FIG. 1F).

Example 4

Effects of an Electrolyte Included in an Anode Chamber on Cell Lysis and/or PCR

In the present Example, in the electrolysis device illustrated in FIG. 1A, a solution including $10^8$ cell/mL E. coli cells in 100 mM NaCl solution was placed into a cathode chamber and 10 mL of each of 100 mM NaCl and 100 mM $Na_2SO_4$ solutions were placed into an anode chamber, and then electrolysis was performed by applying a DC voltage of 5 V for 3 min. After electrolysis, equal amounts of samples were taken from the anode chamber and the cathode chamber and mixed. PCR was performed using the mixture as a template. PCR was performed according to the method described in (3) of Example 1 and Hot-start Taq DNA polymerase (Roche Diagnostics) was used as polymerase.

Figure 13:
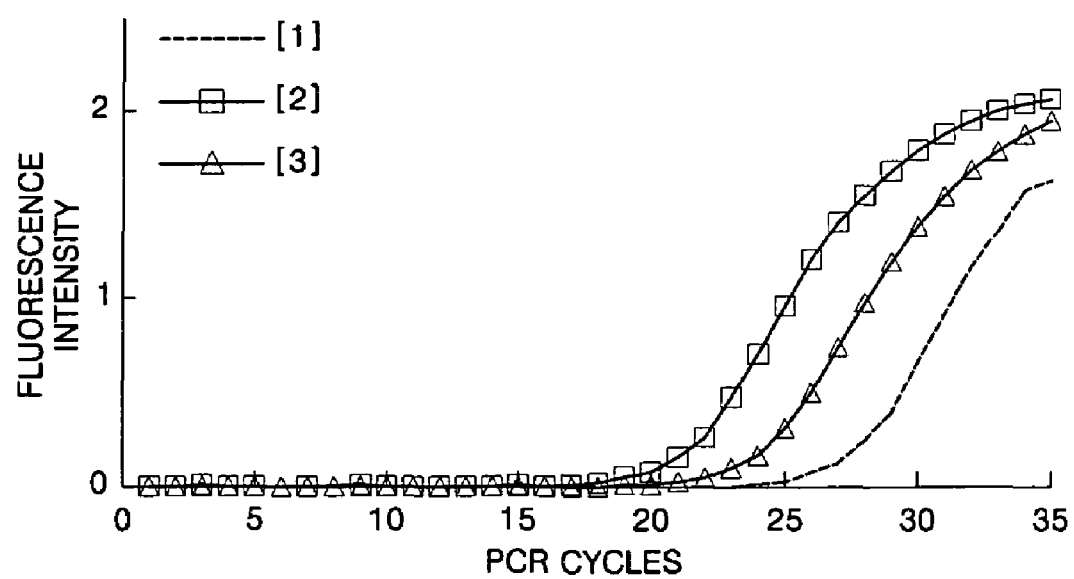
FIG. 13 illustrates the results of a realtime PCR of a mixture of an anode electrolyzed solution and a cathode electrolyzed solution after performing electrolysis using different electrolytes in an anode chamber.

FIG. 13 illustrates the results of realtime PCR performed after causing electrolysis using various electrolytes in the anode chamber and mixing the anode electrolyzed solution and the cathode electrolyzed solution. As shown in FIG. 13, when the anode chamber included $Na_2SO_4$ solution, the initial concentration of nucleic acid and the concentration of final amplified nucleic acid are higher compared to when the anode chamber included NaCl. The results indicate that when the anode chamber includes a material with lower standard oxidation potential than water, it is more advantageous in the subsequent biological analysis and neutralization of an electrolyzed solution.

According to the microfluidic device of the present invention, electrolysis can be performed by applying current while transferring cells to a microchannel to easily lyse cells without using a separate cell lysis solution. Thus, when the microfluidic device is used, since a device for introducing a cell solution is not required, it is simple and is advantageous in miniaturization of a device. Further, the microfluidic device can be used to easily lyse cells.

According to the method of lysing cells or viruses, cells or viruses of the present invention can be easily and efficiently lysed and a cell lysate having pH and electrolyte suitable for the subsequent biological analysis can be prepared.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A microfluidic device comprising an electrolysis device for cell lysis which includes
an anode chamber,
a cathode chamber and
a separator,
wherein the separator is installed between the anode chamber and the cathode chamber, and the separator does not allow ions or gas generated from electrolysis of the electrolyte contained in the anode chamber and the cathode chamber to pass through, and the anode chamber includes an inlet and an outlet for an anode chamber solution and an electrode, and the cathode chamber includes an inlet and an outlet for a cathode chamber solution and an electrode.

2. The microfluidic device of claim 1, wherein the outlet of the anode chamber and the outlet of the cathode chamber are joined to one channel.

3. The microfluidic device of claim 2, wherein the anode chamber solution includes a compound with lower standard oxidation potential than water.

4. The microfluidic device of claim 3, wherein the compound is at least one ion selected from the group consisting of $NO_3^-$, $F^-$, $SO_4^{2-}$, $PO_4^{3-}$ and $CO_3^{2-}$.

5. The microfluidic device of claim 1, wherein the outlet of the anode chamber and the outlet of the cathode chamber are separated.

6. The microfluidic device of claim 5, wherein the anode chamber solution includes a compound with lower or higher standard oxidation reduction potential than water.

7. The microfluidic device of claim 6, wherein the anode chamber solution includes at least one ion selected from the group consisting of $Cl^-$, $NO_3^-$, $F^-$, $SO_4^{2-}$, $PO_4^{3-}$ and $CO_3^{2-}$.

8. The microfluidic device of claim 1, wherein the cathode chamber solution includes cells or viruses.

9. The microfluidic device of claim 1, wherein the cathode chamber solution includes a compound with lower standard reduction potential than water.

10. The niicrofluidic device of claim 8, wherein the solution includes at least one ion selected from the group consisting of $Na^+$, $K^+$, $Ca^{2+}$, $Mg^{2+}$ and $Al^{3+}$.

11. The microfluidic device of claim 1, wherein the separator allows current to pass through and separates ions and gas generated in each chamber due to electrolysis.

12. The micro fluidic device of claim 1, wherein the electrode is selected from the group consisting of Pt, Au, Cu and Pd.

13. The microfluidic device of claim 1, further comprising a pump for introducing and discharging a solution into and from the anode chamber and a pump for introducing and discharging a solution into and from the cathode chamber.

14. The microfluidic device of claim 1, further comprising a pump for introducing and discharging a solution into and from the anode chamber and the cathode chamber.

15. The microfluidic device of claim 1, comprising a cell lysis compartment including the electrolysis device, a nucleic acid isolation compartment, a nucleic acid amplification compartment and a detection compartment.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: artificial sequence
<220> FEATURE:
<223> OTHER INFORMATION: forward primer

<400> SEQUENCE: 1
agtgtggatt cggcactcct                                                    20

<210> SEQ ID NO 2
<211> LENGTH: 23
<212> TYPE: DNA
<213> ORGANISM: artificial sequence
<220> FEATURE:
<223> OTHER INFORMATION: reverse primer

<400> SEQUENCE: 2
gagttcttct tctaggggac ctg                                                23